(12) United States Patent
Riklin Raviv et al.

(10) Patent No.: US 10,147,185 B2
(45) Date of Patent: Dec. 4, 2018

(54) INTERACTIVE SEGMENTATION

(71) Applicants: B.G. NEGEV TECHNOLOGIES AND APPLICATIONS LTD., AT BEN-GURION UNIVERSITY, Beer Sheva (IL); MOR RESEARCH APPLICATIONS LTD., Tel Aviv (IL)

(72) Inventors: Tamar Riklin Raviv, Ramat Gan (IL); Ilan Shelef, Meitar (IL); Itzhak Hershkovich, Kfar Rut (IL); Ohad Chitrit, Dimona (IL)

(73) Assignees: B.G. NEGEV TECHNOLOGIES AND APPLICATIONS LTD., AT BEN-GURION UNIVERSITY, Beer Sheva (IL); MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 15/509,925

(22) PCT Filed: Sep. 8, 2015

(86) PCT No.: PCT/IL2015/050908
§ 371 (c)(1),
(2) Date: Mar. 9, 2017

(87) PCT Pub. No.: WO2016/038604
PCT Pub. Date: Mar. 17, 2016

(65) Prior Publication Data
US 2017/0301085 A1    Oct. 19, 2017

Related U.S. Application Data

(60) Provisional application No. 62/049,006, filed on Sep. 11, 2014.

(51) Int. Cl.
G06K 9/00          (2006.01)
G06T 7/00          (2017.01)
(Continued)

(52) U.S. Cl.
CPC ............ *G06T 7/0012* (2013.01); *G06F 19/00* (2013.01); *G06F 19/321* (2013.01); *G06T 7/12* (2017.01);
(Continued)

(58) Field of Classification Search
None
See application file for complete search history.

(56) References Cited

U.S. PATENT DOCUMENTS 9,401,021 B1 *  7/2016  Biagiotti ............... G06T 7/0014
2017/0091915 A1 *  3/2017  McLaughlin ........... G06T 5/008

OTHER PUBLICATIONS

Tony F. Chan et al, "Active Contours Without Edges", IEEE Transactions on Image Processing, Feb. 2001, vol. 10, No. 2, pp. 266-277.
(Continued)

*Primary Examiner* — Atiba O Fitzpatrick
(74) *Attorney, Agent, or Firm* — The Roy Gross Law Firm, LLC; Roy Gross (57) ABSTRACT

A method for three-dimensional interactive segmentation, including: receiving a three-dimensional medical image of an interior volume of a patient's body; automatically performing three dimensional segmentation on the three dimensional medical image to detect and define a region of interest, wherein the performing of the three dimensional segmentation comprises automatically determining a boundary defining the region of interest; receiving from a user spatial information indicating one or more regions of disagreement in the three-dimensional medical image with respect to the determined boundary; and updating the three dimensional segmentation of the three dimensional medical image based on the spatial information received from the user, wherein the updating comprises updating the determined boundary based on the spatial information to redefine the area of interest.

20 Claims, 7 Drawing Sheets

(51) Int. Cl.
G06F 19/00 (2018.01)
G06T 7/12 (2017.01)
G16H 50/50 (2018.01)

(52) U.S. Cl.
CPC .......... *G16H 50/50* (2018.01); *A61B 2576/00* (2013.01); *G06T 2207/10081* (2013.01); *G06T 2207/10088* (2013.01); *G06T 2207/10132* (2013.01); *G06T 2207/20101* (2013.01); *G06T 2207/20104* (2013.01)

(56) References Cited

OTHER PUBLICATIONS

A. P. Dempster et al, "Maximum Likelihood from Incomplete Data via the EM Algorithm", Journal of the Royal Statistical Society, 1977, vol. 39, No. 1, pp. 1-38.
L. Dice., "Measure of the amount of ecological association between species", Ecological Society of America, Jul. 1945, vol. 26, No. 3, pp. 297-302.
Feng Zhao et al, "An Overview of Interactive Medical Image Segmentation", The Annals of the BMVA, 2013, vol. 2013, No. 7, pp. 1-22.
Y. Gao et al, "A 3D interactive multi-object segmentation tool using local robust statistics driven active contours", Medical Image Analysis, Aug. 2012, vol. 16 No. 6, pp. 1216-1227.
C. Rother et al, ""GrabCur"—Interactive Foreground Extraction using Iterated Graph Cuts", ACM Transactions on Graphics, Aug. 2004, vol. 23, No. 3, pp. 309-314.
P. Karasev et al, "Interactive Medical Image Segmentation Using PDE Control of Active Contours", IEEE Trans Med Imaging, Nov. 2013, vol. 32 No. 11, pp. 2127-2139.
M. Kass et al, "Snakes: Active contour models", International Journal of Computer Vision, Jan. 1988, vol. 1, No. 4, pp. 321-331.
J. Liang et al, "United Snakes", Medical Image Analysis, 2006, vol. 10, pp. 215-233.
K. McGuinness et al, "Toward automated evaluation of interactive segmentation", Computer Vision and Image Understanding, Jun. 2011, vol. 115, No. 6, pp. 868-884.
E. N. Mortensen et al, "Interactive Segmentation with Intelligent Scissors", Graphical Models and Image Processing, Sep. 1998, vol. 60, No. 5, pp. 349-384.
C. Nieuwenhuis et al, "Spatially Varying Color Distributions for Interactive Multilabel Segmentation", IEEE Transactions on Pattern Analysis and Machine Intelligence, May 2013, vol. 35, No. 5, pp. 1234-1247.
S. Osher et al, "Fronts propagating with curvature-dependent speed: Algorithms based on Hamilton-Jacobi formulations", Journal of Computational Physics, Nov. 1988, vol. 79, No. 1, pp. 12-49.
Y. Boykov et al, "Fast Approximate Energy Minimization via Graph Cuts", IEEE Transactions on Pattern Analysis and Machine Intelligence, Nov. 2001, vol. 23, No. 11, pp. 1222-1239.
L. Paulhac et al, "Interactive Segmentation of 3D Images Using a Region Adjacency Graph Representation", 2011, pp. 354-364.
J. S. Prassni et al, "Uncertainty-Aware Guided Volume Segmentation", IEEE Transactions on Visualization and Computer Graphics, Nov.-Dec. 2010, vol. 16, No. 6, 1358-1365.
T. Riklin-Raviv et al, "Segmentation of image ensembles via latent atlases", Medical Image Analysis, Oct. 2010, vol. 14 No. 5, pp. 654-665.
W. Yang et al, "User-Friendly Interactive Image Segmentation Through Unified Combinatorial User Inputs", IEEE Transactions on Image Processing, Sep. 2010, vol. 19, No. 9, pp. 2470-2479.
IMIC_ personal, "Probabilistic model for interactive 3D segmentation 2:15", You Tube-IMIC_personal, [Online], Jun. 12, 2014, Retrieved from the Internet: <URL https://www.youtube.com/watch?v=aRn7TulrWLY>.
N. Ben-Zadok et al, "Interactive level set segmentation for image-guided therapy", IEEE International Symposium on Biomedical Imaging: From Nano to Macro, Jun. 2009, pp. 1079-1082.
See Project: "Probabilistic Model for 3D segmentation 3:29" You Tube—Seg Project Channel, [online], Sep. 5, 2014, Retrieve from the Internet <URL: https://www.youtube.com/watch?v=BF0DiSzFPhl>.
T. Hershkovich et al, "Probabilistic Model for 3D Interactive Segmentation", Computer Vision and Image Understanding, Oct. 2016, vol. 151, pp. 47-60.

* cited by examiner

INTERACTIVE SEGMENTATION

CROSS-REFERENCE TO RELATED APPLICATIONS

This application is a National Phase of PCT Patent Application No. PCT/IL2015/050908 filed Sep. 8, 2015, which claims the benefit of U.S. Provisional Patent Application No. 62/049,006, filed Sep. 11, 2014 and entitled "Interactive Segmentation." The contents of the above application are incorporated herein by reference as if fully set forth in their entirety.

BACKGROUND

The present invention relates to the field of computer vision and to medical imaging analysis in particular.

Image segmentation is fundamental to medical imaging analysis and therefore actively studied, while numerous approaches exist. Recent trends focus on fully automatic segmentation frameworks, being much faster than manual annotation, less biased and repeatable. Usually, the required workload for processing and analyzing large datasets is far behind the ability of a human rater. Moreover, the computational advancements of the machine in cases that require modality fusion or three-dimensional (3D) visualization cannot be competed even by an expert. Nevertheless, as the outcome of the image analysis process might have critical implications on the patient recuperation prospects the expertise of a clinician must be considered.

Interactive segmentation (IS) approaches may be classified based on the form and the type of input provided by the user as well as the underlying segmentation framework (see: F. Zhao, and X. Xie. An overview of interactive medical image segmentation. *Annals of the BMVA*, 7:1-22, 2013). The pioneering IS work, which led to the development of the live wire technique or intelligent scissors (independently suggested by L. Dice. Measure of the amount of ecological association between species. *Ecology*, 26(3):297-302, 1945 and E. N. Mortensen and W. A. Barrett. Interactive segmentation with intelligent scissors. *Graph. Models and Image Proc.*, 60(5): 349-384, 1998) is based on the image edge map. The shortest paths between the user's mouse clicks, calculated by the Dijkstra algorithm form the contour of the region of interest (ROI). In the united snakes (see: J. Liang, T. McInerney, and D. Terzopoulos. United snakes. 10(2): 215-233, 2006), which relies on a classical active contour framework known as snakes (see: M. Kass, A. P. Witkin, and D. Terzopoulos. Snakes: Active contour models. *International Journal of Computer Vision*, 1(4):321-331, Jan. 1988), the user 'plants' anchors or seed points along the desired boundary, providing guidance for the segmentation.

Pointing device scribbles seem to be the most common form of user interaction. Marked regions (e.g., by pointing device scribbles) may provide information about the ROI and the background intensity distributions. A well known IS approach is the GrabCut technique (see: C. Rother, V. Kolmogorov, and A. Blake. Grabcut: Interactive foreground extraction using iterated graph cuts. SIGGRAPH, 2004) which is based on the graph-cut (see: Y. Boykov, O. Veksler, and R. Zabih. Fast approximate energy minimization via graph cuts. *PAMI*, 23(11):1222-1239, 2001). Representing the image pixels by nodes in a graph, the graph-cut addresses a foreground-background image segmentation by solving a min-cut, max-flow problem. The user's annotated regions are assigned to either the source or the sink of the graph. In a recent paper by C. Nieuwenhuis and D. Cremers. Spatially varying color distributions for interactive multilabel segmentation. *PAMI*, 35(5): 1234-1247, 2013, marked user regions, via mouse scribbles were used for gathering spatially varying color statistics for multi-label segmentation. Level-set based segmentation framework with User Interface (UI) which are designed for medical images were suggested in Y. Gao, R. Kikinis, S. Bouix, M. E. Shenton, and A. Tannenbaum. A 3D interactive multi-object segmentation tool using local robust statistics driven active contours. *Medical image analysis*, 16(6):1216-1227, 2012, and P. Karasev, I. Kolesov, K. Fritscher, P. Vela, P. Mitchell, and A. Tannenbaum. Interactive medical image segmentation using PDE control of active contours. 2013. Other recent IS techniques include J. S. Prassni, T. Ropinski, and K Hinrichs. Uncertainty-aware guided volume segmentation. *Visualization and Computer Graphics*, 16(6):1358-1365, 2010; W. Yang, J. Cai, J. Zheng, and J. Luo. User-friendly interactive image segmentation through unified combinatorial user inputs. *TMI*, 19(9):2470-2479, 2010; L. Paulhac, J-Y. Ramel, and T. Renard. Interactive segmentation of 3D images using a region adjacency graph representation. In *Image Analysis and Recognition*, pages 354-364. 2011 and K. McGuinness and N. E. OConnor. Toward automated evaluation of interactive segmentation. *CVIU*, 115(6):868-884, 2011.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising using at least one hardware processor for: receiving a three-dimensional medical image of an interior volume of a patient's body; automatically performing three dimensional segmentation on the three dimensional medical image to detect and define a region of interest in the three dimensional medical image, wherein the performing of the three dimensional segmentation comprises automatically determining a boundary defining the region of interest; receiving an input from a user with respect to the three dimensional segmentation of the three dimensional medical image, wherein the input comprises spatial information indicating one or more regions of disagreement in the three-dimensional medical image with respect to the determined boundary; and updating the three dimensional segmentation of the three dimensional medical image based on the input received from the user, wherein the updating comprises updating the determined boundary based on the spatial information to redefine the area of interest, and wherein the updating is performed according to weights determining the relative contribution of each one of the three dimensional segmentation and the input from the user to the updating of the three dimensional segmentation, thereby determining the extent of influence of the input from the user on the determined boundary.

There is provided, in accordance with another embodiment, a computer program product for 3D interactive segmentation, the computer program product comprising a non-transitory computer-readable storage medium having program code embodied therewith, the program code executable by at least one hardware processor to: automatically perform three dimensional segmentation on the three dimensional medical image to detect and define a region of interest in the three dimensional medical image, wherein the performing of the three dimensional segmentation comprises automatically determining a boundary defining the region of interest; receive an input from a user with respect to the three dimensional segmentation of the three dimensional medical image, wherein the input comprises spatial information indicating one or more regions of disagreement in the three-dimensional medical image with respect to the determined boundary; and update the three dimensional segmentation of the three dimensional medical image based on the input received from the user, wherein the updating comprises updating the determined boundary based on the spatial information to redefine the area of interest, and wherein the updating is performed according to weights determining the relative contribution of each one of the three dimensional segmentation and the input from the user to the updating of the three dimensional segmentation, thereby determining the extent of influence of the input from the user on the determined boundary.

There is provided, in accordance with a further embodiment, a medical system comprising: a medical imaging device; at least one hardware processor configured to: i) automatically perform three dimensional segmentation on the three dimensional medical image to detect and define a region of interest in the three dimensional medical image, wherein the performing of the three dimensional segmentation comprises automatically determining a boundary defining the region of interest; ii) receive an input from a user with respect to the three dimensional segmentation of the three dimensional medical image, wherein the input comprises spatial information indicating one or more regions of disagreement in the three-dimensional medical image with respect to the determined boundary; and iii) update the three dimensional segmentation of the three dimensional medical image based on the input received from the user, wherein the updating comprises updating the determined boundary based on the spatial information to redefine the area of interest, and wherein the updating is performed according to weights determining the relative contribution of each one of the three dimensional segmentation and the input from the user to the updating of the three dimensional segmentation, thereby determining the extent of influence of the input from the user on the determined boundary.

In some embodiments, the three dimensional medical image is of an imaging modality type selected from the group consisting of: Computerized Tomography (CT), Magnetic Resonance Imaging (MM) and ultrasound.

In some embodiments, the method further comprises using said at least one hardware processor for performing three dimensional visualization of the segmented region of interest.

In some embodiments, the method further comprises using said at least one hardware processor for estimating at least one measurable feature of the region of interest.

In some embodiments, the at least one measurable feature is selected from the group consisting of: volume, length, width, height, pose, location and texture.

In some embodiments, the receiving of the input from the user and the updating of the three dimensional segmentation are performed in an iterative manner.

In some embodiments, the receiving of the input from the user is performed via a Graphical User Interface (GUI).

In some embodiments, the GUI presents to the user one or more views of the 3D medical image selected from the group consisting of: slice views in one or more body planes and a 3D view.

In some embodiments, the spatial information comprises anchors indicated by the user via a pointing device on the one or more views of the 3D medical image presented by the GUI.

In some embodiments, the automatically performing of the three dimensional segmentation on the three dimensional medical image to detect and define the region of interest and the updating of the three dimensional segmentation of the three dimensional medical image based on the input received from the user comprises using a probabilistic model.

In some embodiments, the probabilistic model is based on Gaussian Mixture Model (GMM), and wherein the GMM is used to model a distribution of the intensities of the 3D medical image within and outside of the region of interest.

In some embodiments, the performing of the three dimensional segmentation further comprises defining a cost functional, the cost functional comprising: an image likelihood term representing the three dimensional segmentation, and a user interaction term representing the input from the user, assigning the weight of the weights determining the relative contribution of the three dimensional segmentation to the image likelihood term, assigning the weight of the weights determining the relative contribution of the input from the user to the user interaction term, and setting the weight of the weights assigned to the user interaction term to zero.

In some embodiments, the performing of the three dimensional segmentation and the updating the three dimensional segmentation further comprise finding a segmentation that optimizes the cost functional by using a gradient descent process.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION 3D interactive segmentation of medical images is disclosed herein, which provides an automated segmentation algorithm integrated with contextual knowledge, not readily available in the images alone, provided by an experienced physician or another human handler (jointly referred to herein as a "user"). Thus, the disclosed 3D interactive segmentation may provide more accurate segmentation results. Image segmentation in necessary for measuring ROI features, such as size (e.g., volume), pose, location, texture, etc., which may be critical for diagnosis, treatment planning and image-guided therapy. User interaction may be essential for resolving classification ambiguities and errors due to imaging artifacts, poor contrast and noise. The disclosed 3D interactive segmentation of medical images may be utilized, for example, for tumor segmentation for, e.g., fine surgeries, focus ultrasound treatment and the like.

The disclosed 3D interactive segmentation may support an intuitive, convenient and friendly user interaction subjected to the bottom-up constraints introduced by the image intensities. The user may perform a "dialogue" with the segmentation algorithm, for example, via several pointing device inputs in regions of disagreement, formulated as an additional, spatial term in a global cost functional for 3D segmentation. As no prior information may be assumed and the image intensity distribution may be learned throughout the segmentation, the proposed method may be used for a wider range of segmentation applications and imaging modalities.

The disclosed 3D interactive segmentation may provide a user interactive framework for the segmentation of volumetric ROIs. Optionally, a level-set framework may be used, as it is parameterization-free, may allow automatic topological changes and may enable a straightforward generalization to high-dimension and multi-label segmentation. Segmentation may be obtained by solving a maximum a posteriori (MAP) problem. Using calculus of variation, an optimum of a cost functional may be searched, which is based on a generative probabilistic model. An initial, fully automatic segmentation process may be dominated by the gray level distributions of the ROI and the background partitions. A user input, which may be provided by a pointing device or any other input device, may add spatial constraints to the segmentation problem. These constraints are soft and may express, what is termed here the user's certainty disagreement map. The user's disagreement map may be convolved with a Gaussian kernel which may define the local extent of the user influence and may control the level of disagreement (or user's confidence). This contribution may allow establishing a user-machine dialogue. Optionally, the user may not be allowed to edit the segmentation. Instead, the model may provide a framework to refine segmentation by resolving voxel annotation ambiguities, through "negotiation".

The term "medical imaging device" as referred to herein, may relate to a device configured to create visual representations of the interior of a body of a patient for clinical analysis and/or medical intervention. Such device may utilize an imaging modality including Computerized Tomography (CT), Magnetic Resonance Imaging (MM), ultrasound, and/or the like.

The term "3D medical image" or "3D image" as referred to herein, may relate to a set of multiple two-dimensional (2D) scans of different slices of a desired interior volume in a patient's body in multiple body planes (e.g., coronal, sagittal and axial) performed by a medical imaging device. The set of multiple 2D scans may be then combined to produce a 3D model of the interior volume by dedicated software. However, it is intended herein explicitly that the term "3D medical image" covers also non-medical images, such as various industrial images that depict an internal volume of a certain object.

The term "patient" as referred to herein, may relate to any living creature including human beings and animals.

The term "region" as referred to herein, may relate to a 2D region or to a 3D region, according to the specific context. For example, when referring to a region in a scan, which is 2D, then the region is a 2D region. However, when referring to a region in a 3D image or a 3D model, then the region is a 3D region.

The term "region of interest" as referred to herein with respect to a scan or an image (i.e., 3D medical image), may include one or more separate regions in the medical scan or image, which region(s) are expected to encompass an anatomical structure, such as the skull or a tissue, or an abnormality, such as a healthy tissue distorted due to the presence of a tumor, a hemorrhage, a tumor and/or the like.

The term "boundary" as referred to herein with respect to an ROI defined in a medical image or a scan, may relate to a boundary delimiting the ROI in the medical image or the scan. Such boundary may include each separate boundary which delimits each separate region of the ROI. The boundary may be a line consisting of pixels (e.g., when defined in a 2D scan) or of a surface consisting of voxels (e.g., when defined in a 3D image).

Figure 1:
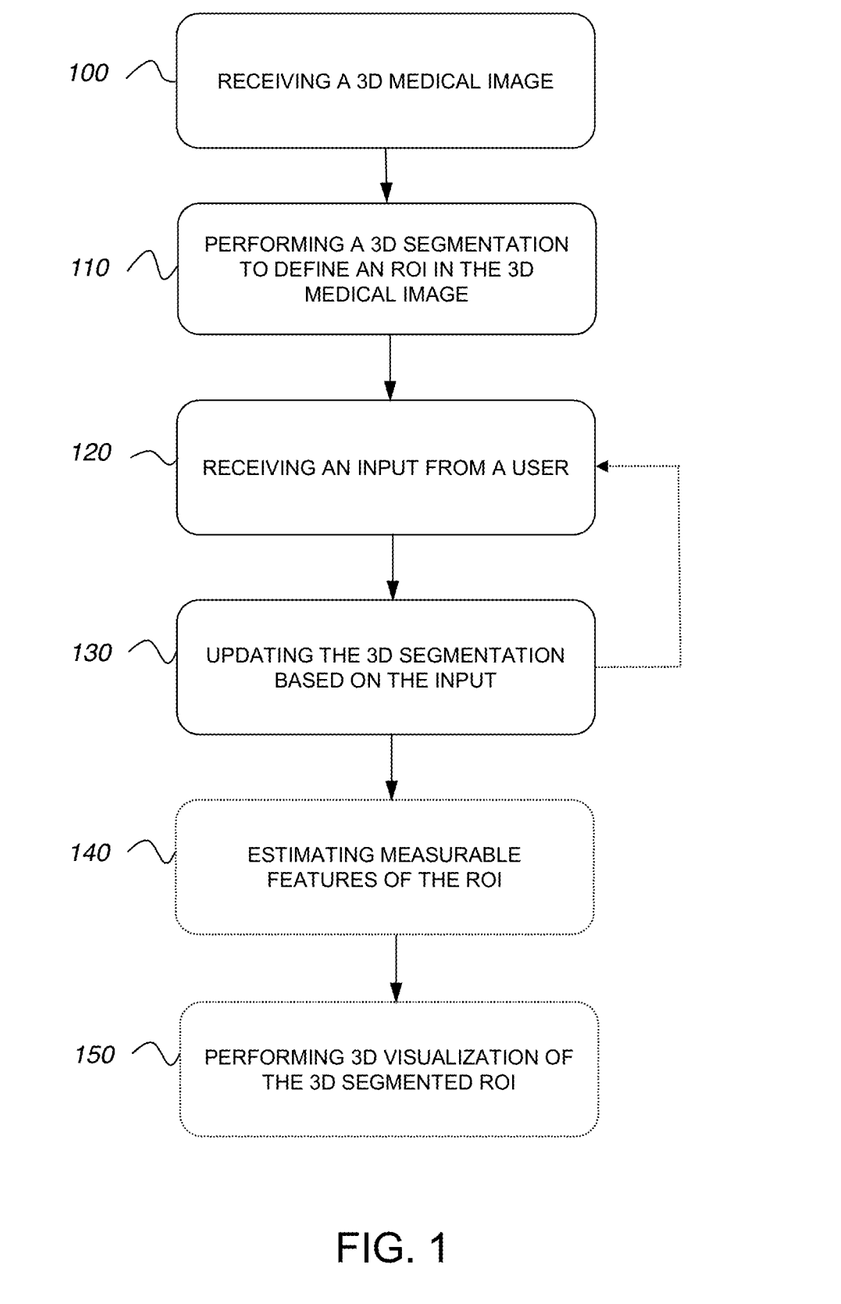
FIG. 1 shows a flowchart of a method for performing a 3D interactive segmentation, constructed and operative in accordance with an embodiment of the disclosed techniques.

Reference is now made to FIG. 1, which shows a flowchart of a method for performing a 3D interactive segmentation, constructed and operative in accordance with an embodiment of the disclosed techniques.

In a step 100, a 3D medical image of an interior volume of a patient's body may be received. The 3D medical image may be of an imaging modality type, such as Computerized Tomography (CT), Magnetic Resonance Imaging (Mill) and ultrasound. The 3D medical image may include a set of multiple two-dimensional (2D) scans of different slices of the interior volume.

In a step 110, 3D segmentation may be automatically performed on the 3D medical image to detect and define a region of interest (ROI) in the 3D medical image. The segmentation may include automatically determining a boundary around the ROI. Various methods of the prior art may be used to perform the 3D segmentation. Alternatively, the segmentation method laid out below may be used.

In some embodiments, the segmentation may be performed by estimating the probability of voxels of the 3D medical image to be within or outside of the ROI, where each voxel may be characterized by intensity. Accordingly, the automatically performing of the 3D segmentation may include using a probabilistic model. The probabilistic model may be based on Gaussian Mixture Model (GMM). The GMM may be used to model a distribution of the intensities of the 3D medical image within and outside of the ROI. The automatic performing of the 3D segmentation may include defining a cost functional. The cost functional may include an image likelihood term representing the three dimensional segmentation and a user interaction term representing the user input. Optionally, the cost functional may further include a regularization term representing segmentation smoothness constraints.

The cost functional may be formulated according to a level-set framework and in a continuous form. Weights may be assigned to the image likelihood term and to the user interaction term determining the relative contribution of each term to the 3D segmentation. The regularization term may be also assigned a weight. Accordingly, at this stage, the weight assigned to the user interaction term may be set to zero.

A segmentation which optimizes the cost functional may be found via a gradient descent process. A probability map of the image voxels to be within or outside of the ROI may be then determined. In some embodiments, a probability threshold may be defined in order to deterministically define the ROI. This may be performed by comparing the probability of each voxel to the threshold in order to determine if the voxel belongs to the ROI or to the background. Then, a boundary of the ROI, resulting from the application of the threshold, may be displayed to the user. Optionally, the boundary is shown superimposed on the medical image. The probability threshold may be set, for example, to 0.5.

In a step 120, an input with respect to the 3D segmentation of the ROI may be received from a user. The user may advantageously be a physician or any other medical specialist. The input may include spatial information, e.g., indicating one or more regions of disagreement in the three-dimensional medical image with respect to the determined boundary. Thus, for example, the user may disagree with the determination (e.g., according to the automatically performed 3D segmentation of step 110) that a specific region is included in the background or in the ROI (i.e., as defined by the determined boundary). The spatial information provided by the user may not be accurate, in order to not burden the user. Thus, the user may indicate regions and not necessarily exact locations. The user input may add spatial constraints to the fully automatic segmentation process of step 110, which may be dominated by the gray level distributions of the 3D image. Advantageously, since the user input is spatial (as opposed to input relating to the grey levels), it may influence the automatic segmentation process based on the grey level distribution of the 3D image in only a local and specific manner.

Figure 2A:
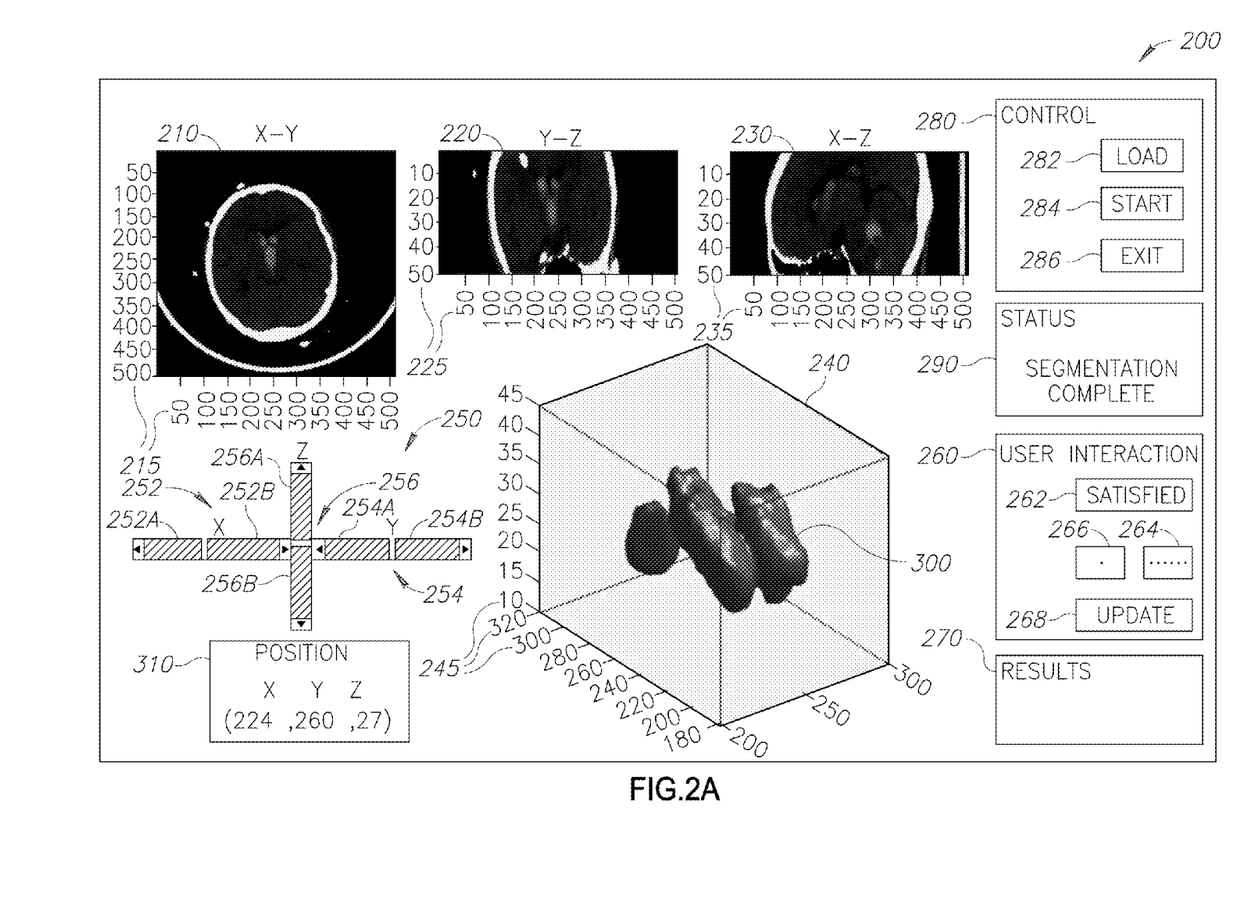
FIG. 2A shows a screen shot of an exemplary Graphical User Interface (GUI) presenting views of a segmented 3D medical image.

In some embodiments, the input from the user may be received via a GUI. Reference is now made to FIG. 2A, which shows a screen shot of an exemplary GUI 200, which presents views of a segmented 3D medical image. The 3D medical image is of a human brain which includes a cerebral hemorrhage (CH). The CH may be segmented (i.e., ROI) according to step 110. GUI 200 may include one or more views of or deriving from the 3D medical image, such as slice views 210, 220 and 230 and a 3D view 240. Slice views 210, 220 and 230 may present to the user the 2D scans of the different slices of the interior volume. Slice view 210 may present scans in X-Y body planes (i.e., coronal planes), slice view 220 may present scans in Y-Z body planes (i.e., sagittal planes) and slice view 230 may present scans in X-Z body planes (i.e., axial planes). 3D view 240 may present a 3D model 300 of the segmented area of interest. Alternatively or additionally, 3D view 240 may present a 3D model of the entire interior volume, and/or of other portions of the interior volume.

GUI 200 may include notations 215, 225, 235 and 245 for slice views 210, 220 and 230 and 3D view 240, correspondingly, which may indicate the relative position of elements in the scans or of the 3D model within the 3D medical image. GUI 200 may further include a 3D scroll bar 250 which may allow the user to scroll through scans in a selected body plane. 3D scroll bar may include X scroll bars 252, Y scroll bars 254, and Z scroll bars 256. X scroll bars may include a left scroll bar 252A and a right scroll bar 252B. Y scroll bars may include a left scroll bar 254A and a right scroll bar 254B. Z scroll bars may include an up scroll bar 256A and a down scroll bar 256B. For example, the user may scroll through all of the 2D scans of the 3D medical image which are in a coronal plane by clicking Z bars 256. The user may go up along an axis Z of the 3D medical image by clicking the up scroll bar 256A or down along the axis by clicking down scroll bar 256B. The scans may be shown in slice view 210. GUI 200 may further include a position tag 310, which may indicate a current position of each one of the 2D scans shown in slice views 210 (along the z axis), 220 (along the x axis) and 230 (along the y axis).

GUI 200 may further allow the user to rotate 3D model 300 in a plurality of directions, optionally in all directions. The user may rotate 3D model 300 by an input device such as a mouse.

Figure 2B:
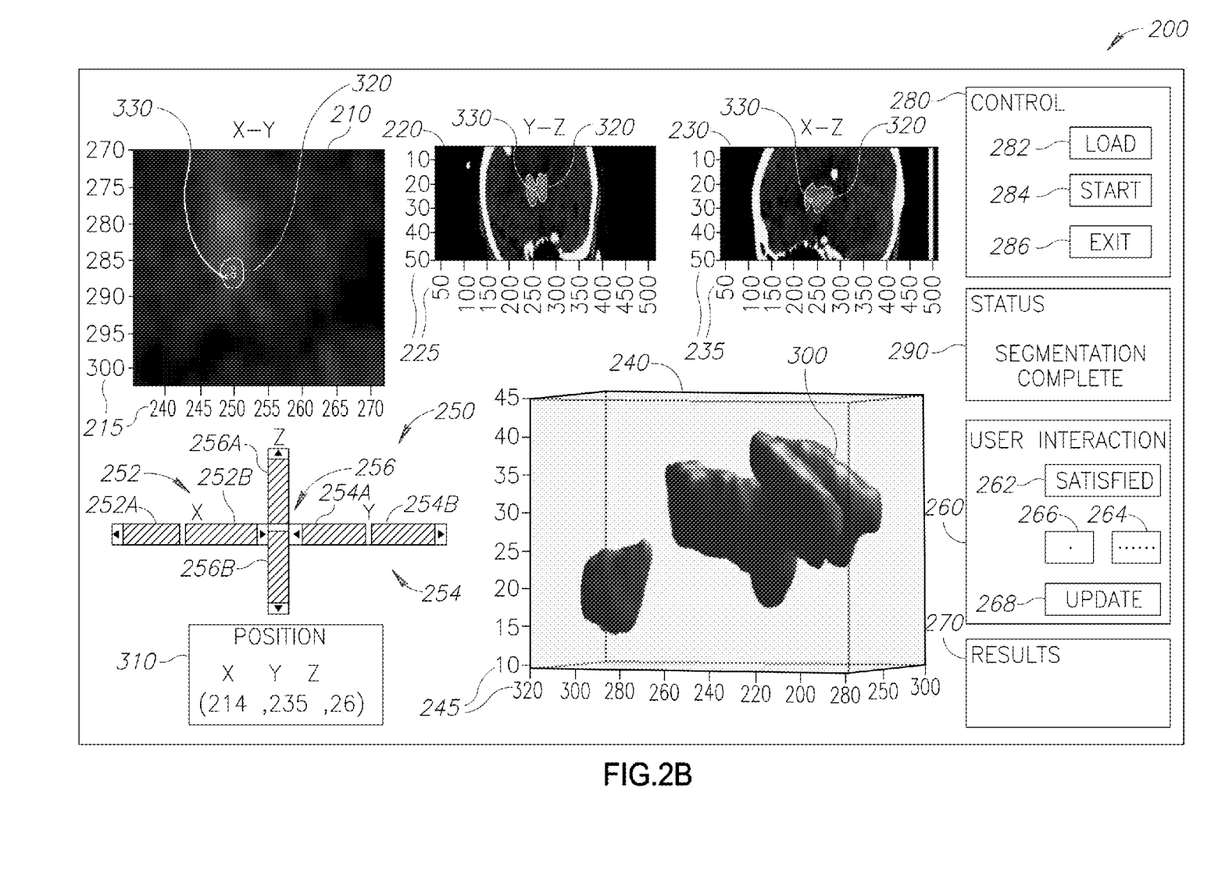
FIG. 2B shows a screen shot of the GUI of FIG. 2A including a user input with respect to the segmentation of the 3D medical image.
Figure 3A:
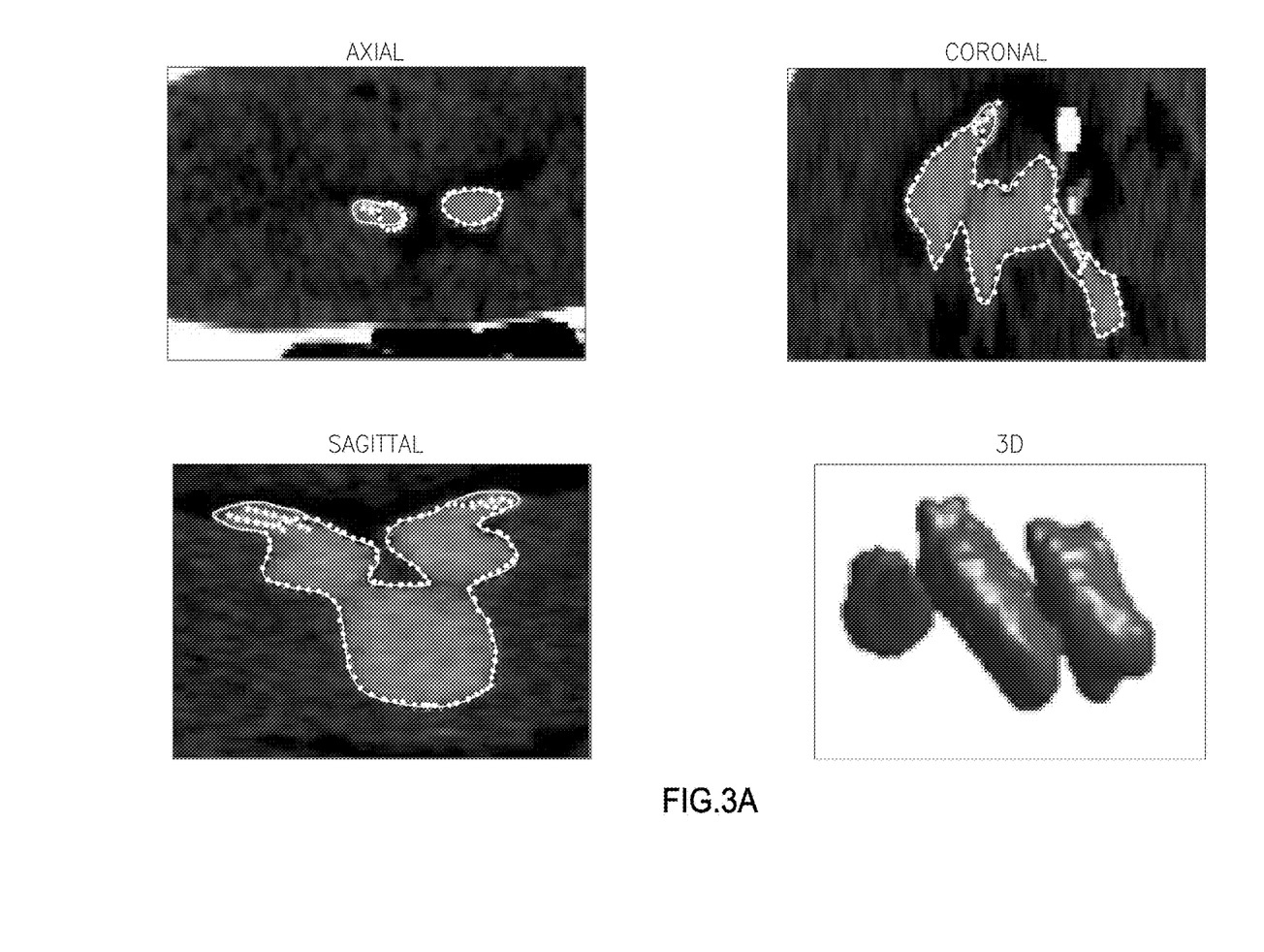
FIGS. 3A-3D show various views of a Computerized Tomography (CT) 3D medical image of CH in a human brain of various patients segmented according to the disclosed probabilistic model.
Figure 3B:
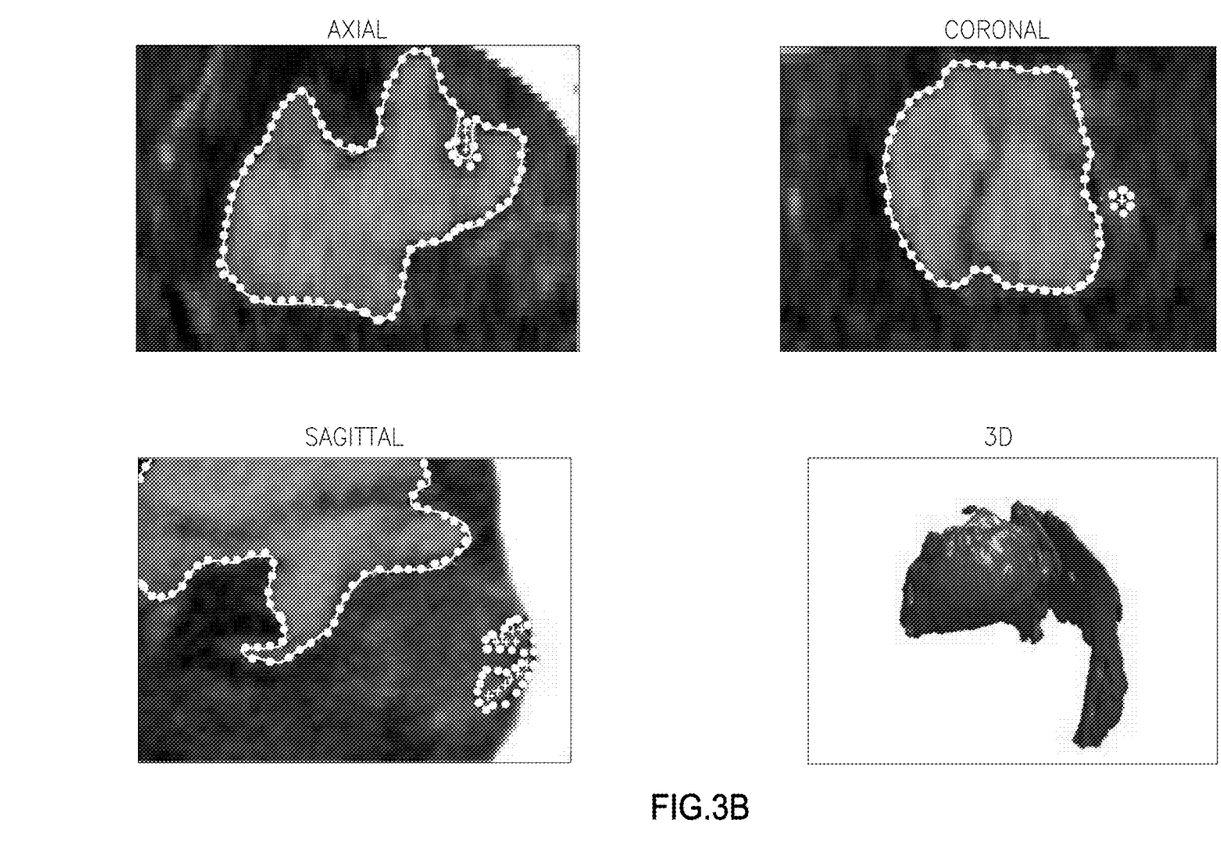
Figure 3C:
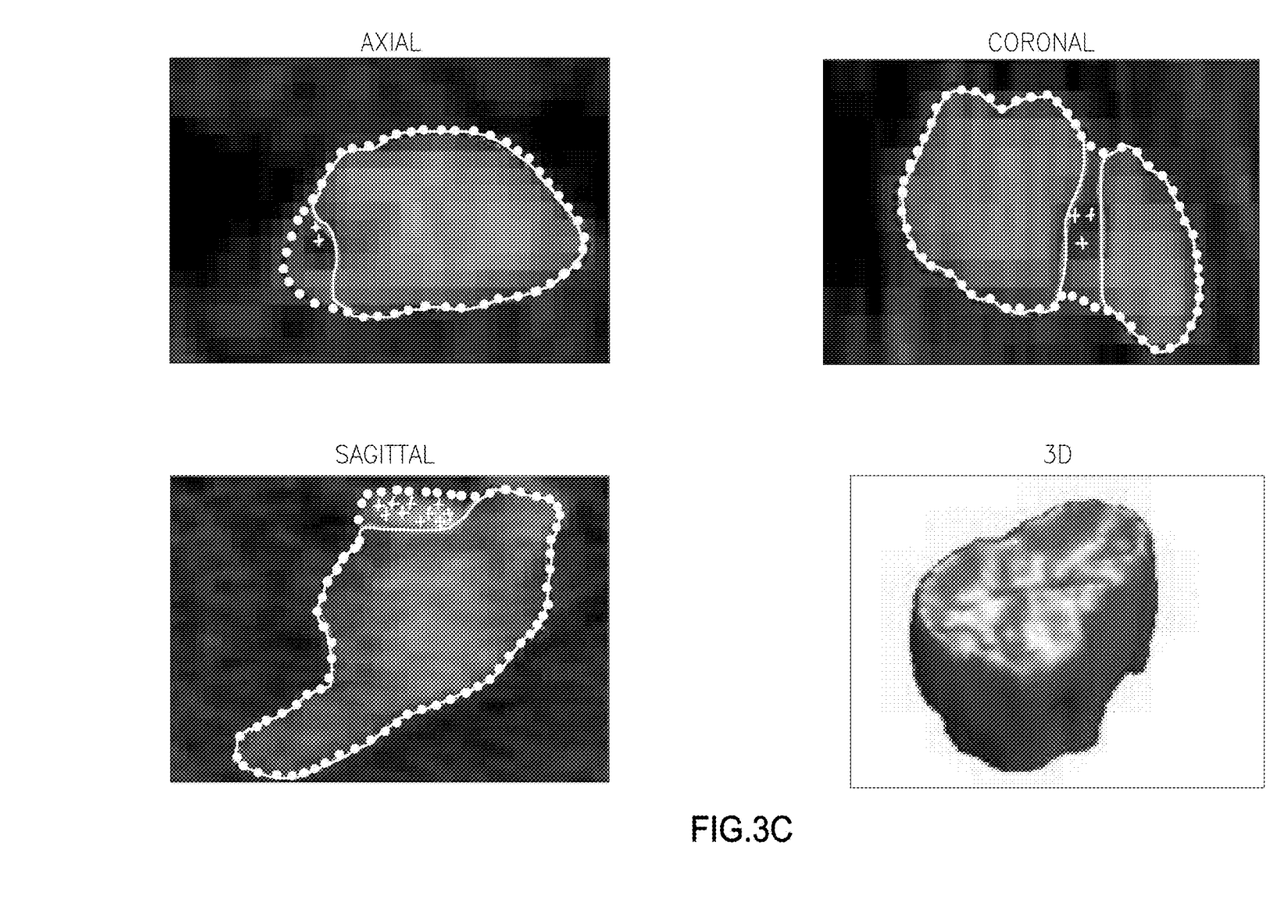
Figure 3D:
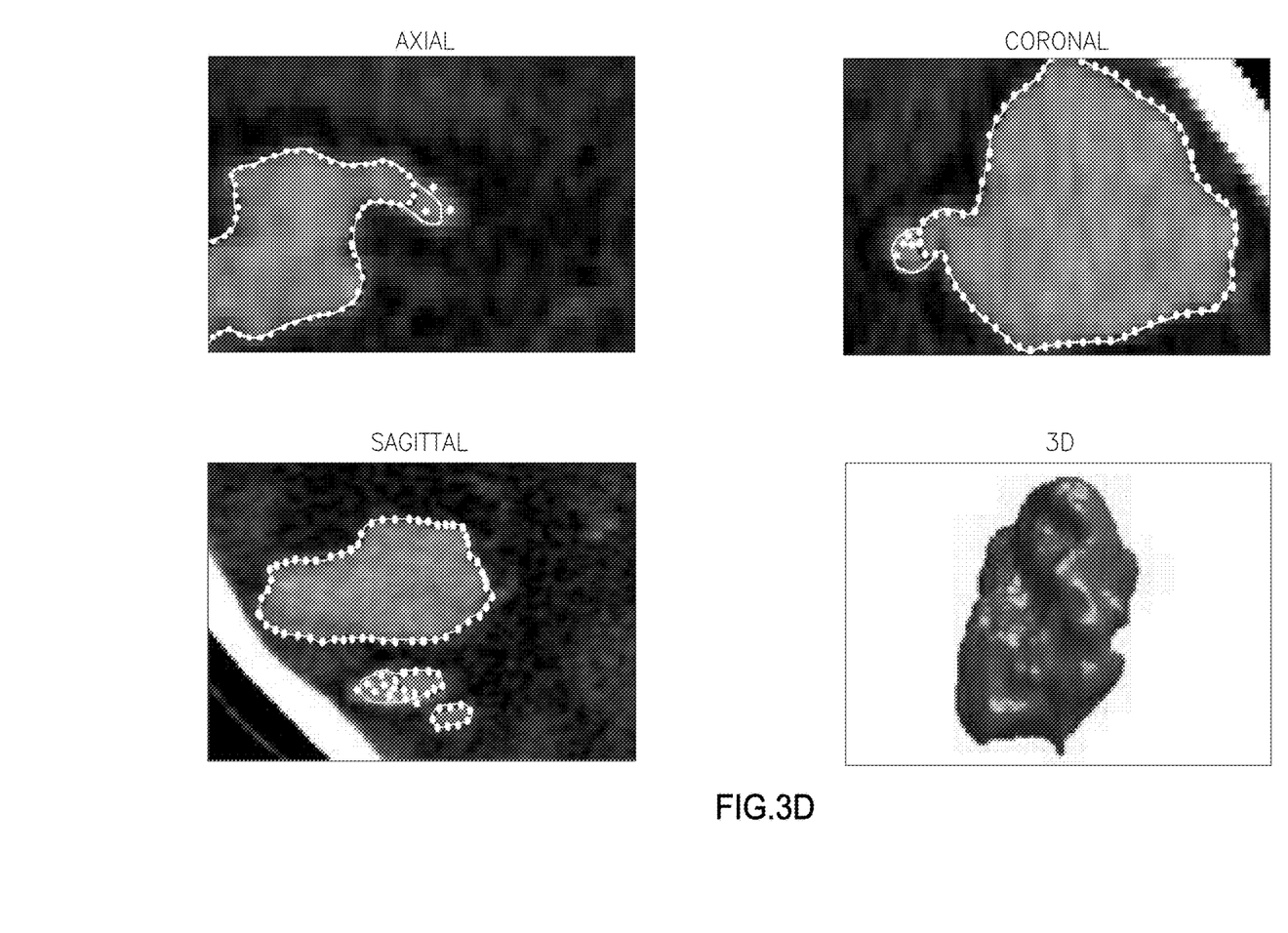

In some embodiments, the spatial information may include anchors indicating a spatial region within the 3D medical image. The anchors may be indicated on one or more views of the 3D medical image presented by GUI 200. Reference is now made to FIG. 2B, which shows a screen shot of GUI 200 of FIG. 2A including a user input with respect to the segmentation of the 3D medical image. The segmentation of the 3D medical image according to step 110 may be presented to the user by a boundary line 320, for example, of a specific color, segmenting the CH. The user may then define a region of disagreement by anchors, which may be indicated, for example, via a pointing device (e.g., a mouse or a touchpad) by pointing on one or more views of the 3D medical image, or via any other input device, such as a keyboard or a touch screen. For example, anchors may be located by the user on a view of the 3D medical image to indicate a region to be added to the segmented ROI (i.e., a region of disagreement). In this manner, the user may indicate that the determined boundary should also delimit the region defined by the located anchors. As another example, anchors may be located to indicate a region to be removed from a segmented ROI (i.e., a region of disagreement). In this manner, the user may indicate that the determined boundary should not delimit the region defined by the located anchors. The anchors may be represented by GUI 200 as asterisks 330 and may differ, for example, by color or shape, in order to distinguish between anchors which define a region to be added to the segmented ROI and anchors which define a region to be removed from the segmented ROI.

GUI 200 may further include user interaction buttons 260, a results tag 270, control buttons 280 and a status tag 290. User interaction buttons 260 may allow the user to interact or have a 'dialogue' with the segmentation process. For example, the user may indicate that the segmentation is satisfying by pressing a 'satisfied' button 262, add an input (i.e., according to step 120) by pressing input buttons 264 and 266 or update the segmentation of the 3D medical image (i.e., according to step 130 below) by pressing an update button 268. Input button 266 may allow the user to add anchors to the segmented 3D image (e.g., by locating asterisks or plus signs on the presented 2D scans of the 3D medical image). Input button 264 may allow the user to add a line defined by a sequence of anchors. Results tag 270 may present to the user the values of measured features of the defined ROI (see step 140 below), such as volume or other size dimensions (i.e., length, width and height) pose (i.e., the exact location of the center of mass), location, texture (i.e., by applying a sequence of filters which may produce values that may characterize particular textures), etc. User control buttons 280 may include buttons which allow the user to perform various operations such as load a 3D medical image by pressing a load button 282 (e.g., by clicking or touching on an input device or touching the button itself as presented on the screen), start a segmentation process by pressing a start button 284 and exit the GUI and the segmentation process by pressing on an exit button 286. Status tag 290 may show the status of the entire segmentation process, which may be an iterative process, e.g., by indicating that segmentation (i.e., a segmentation iteration) is complete. GUI 200 may additionally allow the user to enlarge or reduce slice views 210, 220 and 230 and/or 3D view 240.

In a step 130, the 3D segmentation of the region of interest may be updated based on the input received from the user. For example, and with reference to FIG. 2A, the user may press update button 268 in order to initiate or execute the update process. Alternatively, the updating process may be initiated automatically once an input from the user is received. Optionally, the update may be performed according to the GMM-based probabilistic model. At this stage, the weight assigned to the user interaction term may be set to a predefined or a selected value higher than zero. The weight assigned to the user interaction term may determine the extent of the user's influence, i.e., the influence of the user's input on the automatic segmentation. The user may not edit the determined boundary. Such an approach takes into account human error and is more user friendly since it may allow the user to provide spatial information which is not necessarily accurate. This weight value of the user input at this stage may be selected by the user or may be predefined.

Optionally, the weight assigned to the regularization may be set, at this stage, to a value which is lower than its value at the automatic segmentation stage (i.e., step 110) or may be set to zero. Optionally, the user input may be integrated with the determined 3D segmentation in a probabilistic manner according to the probabilistic model indicated above. A 3D segmentation which may optimize the cost functional may be found by using a gradient descent process. A more detailed description of the updating of the 3D segmentation according to this technique is provided herein below.

In some embodiments, the receiving of the input from the user with respect to the 3D segmentation of the region of interest and the updating of the 3D segmentation of the region of interest based on the input received from the user may be performed in an iterative manner. Thus, the user may keep providing input and following that, the segmentation of the ROI may be updated until the user is satisfied from the results. The iterations may allow the user to amend his errors. Furthermore, the iterations may allow the user, ultimately, to provide a more accurate input achieved in a manner which is more convenient and user-friendly. In addition, the iterations may allow the user to bestow his input more weight than originally given, in case the weight of the user input is predefined.

At the first iteration, a first fully automatic segmentation is performed according to step 110. A first update according to a first user input may be performed with respect to the fully automatic segmentation (according to step 130). At the next iterations, the update is performed with respect to the current determined segmentation (i.e., as previously updated). According to experimental results, the overall number of interaction steps needed was in general not higher than two, but further iterations, if needed, may be performed.

In an optional step 140, measurable features of the ROI may be estimated. Such features may include: size features such as volume, pose, location, texture, etc. The estimation of such features may be presented to the user, for example, in results tag 270 of GUI 200 of FIG. 2A.

In an optional step 150, a 3D visualization of the segmented ROI may be performed. For example, via GUI 200 and such as 3D model 300.

A medical system for performing interactive 3D segmentation is herein disclosed. The medical system may include a medical imaging device and at least one hardware processor. The medical imaging device may be configured to capture the 3D medical image of an interior volume of a patient's body and the at least one hardware processor may be configured to interactively segment a region of interest of the captured 3D medical image according to the method of FIG. 1 and the techniques disclosed herein. The medical system may further include a non-transitory storage medium which may store the captured 3D medical image. The medical imaging device may be as known in the art, and such as a CT device, an MM device or an ultrasound device.

A probabilistic model based on GMM, which may be used for 3D interactive segmentation of the ROI, is disclosed herein below. At first, a definition and formulation of the problem presented by the disclosed 3D interactive segmentation is described.

Let I be a gray-level image defined on a 3D image domain $\Omega$. The goal is to find the ROI/background image partitions denoted by $\omega$ and $\Omega \backslash \omega$, respectively. Let $S:\Omega \rightarrow \{0,1\}$ denote the unknown binary voxel annotation of I corresponding to this partition. One may assume that the observed image I is generated such that each image voxel is independent and identically distributed random variable (i.i.d) by the respective segmentation S with probability $p(I|S; \psi)$ where $\psi$ are GMM parameters of image intensities. A fully automatic segmentation may be stated as a MAP problem:

$$p(S|I;\psi) \propto p(I|S;\psi)p(S), \quad (1)$$

where the prior $p(S)$ is used for regularization as one shall see in the following. Incorporating the user input, the proposed segmentation framework may be carried out in a step-by-step manner, where at each step k the user provides a set of spatial parameters through the interaction, after observing the previous segmentation estimate, i.e. $S^{k-1}$. This set may be denoted by $\eta^k$ and one may assume that $S^k$ is generated with probability $p(S^k|S^{k-1};\eta^k)$. One should note that the similarity of this conditional probability to a first order Markov chain where $\eta^k$ may be considered as the transition probability parameters. Given $S^{k-1}$, the intensity distribution parameters of the observed image, denoted by $\psi$ and the user input, i.e. $\eta^k$, one may define the posterior probability of $S^k$, using the Bayes theorem and the chain rule, as follows:

$$p(S^k|I,S^{k-1};\psi,\eta^k) \propto p(I|S^k;\psi)p(S^k|S^{k-1};\eta^k). \quad (2)$$

One may look for $\hat{S}^k = \text{argmax}_{S^k} p(S^k|I,S^{k-1};\psi,\eta^k)$ by minimizing the following cost functional:

$$\in = -\log p(I|S^k;\psi) - \log p(S^k|S^{k-1};\eta^k), \quad (3)$$

using the proportion $\in \propto -\log p$. In the following, an explicit formulation of the image likelihood term $p(I|S^k;\psi)$ to and the user input term $p(S^k|S^{k-1};\eta)$ will be presented. One may assume i.i.d. distribution of the image voxels. Therefore the probability over the entire image domain will be presented by the product of probabilities of each voxel. A continuous form of $\in$, based on a level-set framework will be introduced next, followed by a gradient descent optimization process to estimate $S^k$.

Mixtures of Gaussians may be used to model the intensity distribution within and outside the ROI. Let $\psi_{in} = \{\mu_i^{in}, \sigma_i^{in}, w_i^{in}\}_{i=1}^{N^{in}}$ and let $\psi_{out} = \{\mu_i^{out}, \sigma_i^{out}, w_i^{out}\}_{i=1}^{N^{out}}$, where $N^{in}$ and $N^{out}$ are the respective numbers of Gaussians and $w_i$ are the weights. For each image voxel x with intensity I(x) one may define:

$$P_{in}(x) \propto \sum_{i=1}^{N^{in}} w_i^{in} \exp\left(-\frac{(I(x)-\mu_i^{in})^2}{(\sigma_i^{in})^2}\right) \text{ and}$$

$$P_{out}(x) \propto \sum_{i=1}^{N^{out}} w_i^{out} \exp\left(-\frac{(I(x)-\mu_i^{out})^2}{(\sigma_i^{out})^2}\right).$$

The image likelihood cost, for a given ROI, may be defined as follows:

$$\varepsilon_{IL} = -\sum_{x \in \omega^k} \log P_{in}(I(x), \psi_{in}) - \sum_{x \in \Omega \setminus \omega^k} \log P_{out}(I(x), \psi_{out}) \quad (4)$$

$$= -\sum_{x \in \Omega} [S^k(x) \log P_{in}(I(x), \psi_{in}) + (1-S^k(x)) \log P_{out}(I(x), \psi_{out})]$$

One should note that both the ROI (or equivalently, the segmentation $S^k$) and the intensity parameters $\psi$ are unknown, and are therefore estimated via an alternating minimization scheme which will be detailed in the following.

For example, by using mouse clicks, the user may indicate disagreement with the current segmentation. The collection of user clicks at a time step k may be considered as a forest of impulse responses $U^k = \sum_{m=1}^{M^k} \delta(x_m^k)$ defined on the 3D image domain, where $x_m^k = (x_m^k, y_m^k, z_m^k)$ are the coordinates of a marked voxel and $M^K$ is the number of clicks at time step k. Let $\hat{\omega}^{k-1}$ be the ROI estimate at step k-1. One may then define $p(S^{k-1}(x)) \triangleq p(x \in \hat{\omega}^{k-1})$. To the first approximation, the transition probability, given the user input may take the following form:

$$p(S^k \mid S^{k-1}; U^k) = \begin{cases} p(S^{k-1}) & \text{if } U^k = 0 \\ 1 - p(S^{k-1}) & \text{if } U^k = 1 \end{cases}. \quad (5)$$

or, alternatively, $$p(S^k|S^{k-1};U^k) = p(S^{k-1})^{(1-U^k)}(1-p(S^{k-1}))^{U^k} \quad (6)$$

In practice, one may smooth the binary user input by a convolution with a Gaussian kernel: $\eta^k \triangleq U^k * G_{\sigma^u}$. The transition probability may now be rephrased as follows:

$$p(S^k|S^{k-1};\eta^k) = p(S^{k-1})^{(1-\eta^k)}(1-p(S^{k-1}))^{\eta^k}. \quad (7)$$

One should note that the voxels background/foreground assignments are not altered due to the user input. Instead, the assignment probability of a voxel at x may be flipped with probability $\eta^k(x)$, where $\eta^k$ represents the user's confidence or certainty disagreement map at step k. The extent of the user's influence, i.e., au, may be either determined by the user or set to a default value. To avoid cases in which a user click within the ROI affects the background or vice versa one may define ROI-background user maps as follows: $\eta_{in}^k = S^{k-1}\eta^k$ and $\eta_{out}^k = (1-S^{k-1})\eta^k$. One may now define a user interaction energy term as a sum of two components referring to the user's clicks within the ROI and outside it:

$$\varepsilon_{UI} = -\sum_{x \in \omega^k} \log_{in} p(S^{k-1}(x), \eta_{in}^k(x)) - \quad (8)$$

-continued $$\sum_{x \in \Omega \setminus \omega^k} \log p_{out}(S^{k-1}(x), \eta_{out}^{(k)}(x))$$

$$= -\sum_{x \in \Omega} \left[ \begin{array}{l} S^k(x) \log p_{in}(S^{k-1}(x), \eta_{in}^k) + \\ (1-S^k(x)) \log p_{out}(S^{k-1}(x); \eta_{out}^k) \end{array} \right],$$

where, $\log p_{in}(S^{k-1},\eta^k_{in}) \triangleq \log p(S^k|S^{k-1};\eta^k_{in})$, and $\log p_{out}(S^{k-1},\eta^k_{out}) \triangleq \log p(S^k|S^{k-1};\eta^k_{out})$, are defined by Eq. (7).

One may use a level-set framework to formulate the user-interface-segmentation problem (see: S. Osher and J. A. Sethian. Fronts propagating with curvature-dependent speed: Algorithms based on Hamilton-Jacobi formulations. *Journal of Computational Physics,* 79:12-49, 1988). Let $\phi^k$ define a level-set function, such that $\delta \omega^k = \{x|\phi^k(x)=0\}$ may denote the estimated ROI boundaries in I at step k, and let $\omega_k$ denote the corresponding ROI domain. As in: T. F. Chan and L. A. Vese. Active contours without edges. *TIP,* 10(2): 266-277, 2001, the binary segmentation $S^k$ may be represented by applying the Heaviside function to $\phi^k$, i.e. $H(\phi^k)$. Adopting the probabilistic approach in T. Riklin Raviv, K. Van Leemput, B. H. Menze, W. M. Wells, and P. Golland. Segmentation of image ensembles via latent atlases. *Medical Image Analysis,* 14(5):654-665, 2010, one may use the logistic regression sigmoid, which may be used as a regularized form of the Heaviside function, to represent the soft segmentation $p(S^k)$:

$$H_\varepsilon(\phi^k) = \frac{1}{2}\left(1+\tanh\left(\frac{\phi^k}{2\varepsilon}\right)\right) = \frac{1}{1+e^{-\phi^k/\varepsilon}}, \quad (9)$$

where $\in$ may be used to determine the fuzziness of the estimated ROI boundaries (see: T. Riklin Raviv, K. Van Leemput, B. H. Menze, W. M. Wells, and P. Golland. Segmentation of image ensembles via latent atlases. *Medical Image Analysis,* 14(5):654-665, 2010). As is in the aforementioned Raviv et al., one may now define the level-set function $\phi^k$, as follows:

$$\phi^k(x) \triangleq \varepsilon \text{logit}(p) = \varepsilon \log \frac{p(x \in \omega^k)}{1-p(x \in \omega^k)} = \varepsilon \log \frac{p(x \in \omega^k)}{p(x \in \Omega \setminus \omega^k)}. \quad (10)$$

It may be shown by substitution of Eq. (10) into Eq. (9) that $H_\in(\phi^k)$ is equivalent to $p(x \in \omega^k)$. This relation is fundamental in the proposed probabilistic level-set framework. It is important to note that $\phi^k$ is generated in an iterative manner, using a gradient descent framework. However, k is not an iteration index (which will be denoted by $\tau$) but the final form of a level-set function after a first step of fully automatic segmentation followed by k-1 steps of user interaction. The number of steps may be not higher than two or three. Next, one may use the equivalence between $p(S^k)$ and $H_\in(\phi^k)$, and the continuous forms of the equations above to resolve the segmentation problem via a level-set based gradient descent optimization.

The proposed cost functional for level-set based segmentation includes an image likelihood term, $\in_{IL}$, a regularization term, $\in_{REG}$, and a user interaction term $\in_{UI}$:

$$\in(\phi^k|I,\phi^{k-1},\psi\eta^k) = \in_{IL}(\phi^k|I,\psi) + \in_{UI}(\phi^k|\phi^{k-1},\eta^k) + \in_{REG}(\phi^k) \quad (11)$$

Adopting a continuous formulation and a soft definition of the ROI, the sum over the image voxels, i.e., $\Sigma_x \in \Omega$, is replaced with an integration: $\int_\Omega dx$, and the binary segmentation $S^k(x)$ is replaced by the probability that a voxel x belongs to the ROI: $p(S^k(x))$ or, using the level-set formulation, by $H_\in(\phi^k(x))$. The explicit form of the energy functional in Eq. (11) is as follows:

$$\varepsilon(\phi^k) = \int_\Omega W_{UI}[H_\varepsilon(\phi^k(x))\log p_{in}(\eta_{in}^k) + H_\varepsilon(-\phi^k(x))\log p_{out}(\eta_{out}^k)] + \quad (12)$$

$$W_{IL}[H_\varepsilon(\phi^k(x))\log p_{in}(I;\psi_{in}) + H_\varepsilon(-\phi^k(x))\log p_{out}(I;\psi_{out})] +$$

$$W_{LEN}|\nabla H_\varepsilon(\phi^k(x))|dx.$$

The last term in Eq. (12), i.e. $|\nabla H_\in(\phi^k(x))|$, is known, in the level-set literature as the smoothness or regularization term (see: T. F. Chan and L. A. Vese. Active contours without edges. *TIP*, 10(2):266-277, 2001). The relation to $-\log p(S^k)$ where $p(S^k)$ is the prior in Eq. (1) is shown in: T. Riklin Raviv, K. Van Leemput, B. H. Menze, W. M. Wells, and P. Golland. Segmentation of image ensembles via latent atlases. *Medical Image Analysis*, 14(5):654-665, 2010. The weights $W_{UI}$, $W_{IL}$, $W_{LEN}$, may be positive scalars that balance the contribution of each term. In the first, fully automatic segmentation phase $W_{UI}$ is set to zero. Similarly, $W_{LEN}$ may be set to a lower value (or zero) in the presence of user interaction.

One may look for the segmentation $\phi^k$ that optimizes the energy functional Eq. (12) via a gradient descent process:

$$\phi_{\tau+\Delta\tau}^k = \phi_\tau^k + \Delta\tau \frac{\partial \phi^k}{\partial \tau},$$

where, $\phi_\tau^k$ is the level-set estimate at iteration $\tau$ in step k. The gradient descent step $$\frac{\partial \phi^k}{\partial \tau}$$

may be derived from the first variation of the functional above and may determine the evolution of the segmentation:

$$\frac{\partial \phi^k}{\partial \tau} = \delta_\varepsilon(\phi^k)\left\{W_{UI}[\log p_{in}(\eta_{in}^k) - \log p_{out}(\eta_{out}^k)] + \quad (13)\right.$$

$$\left. W_{IL}[\log p_{in}(I;\psi_{in}) - \log p_{out}(I;\psi_{out})] + W_{LEN}div\left(\frac{\nabla \phi^k}{|\nabla \phi^k|}\right)\right\},$$

where, div is the divergence operator and $\delta_\in(\phi^k)$ is the derivative of $H_\in(\phi^k)$ with respect to $\phi^k$:

$$\delta_\varepsilon(\phi) = \frac{dH_\varepsilon(\phi)}{d\phi} = \frac{1}{4\varepsilon}sech^2\left(\frac{\phi}{2\varepsilon}\right).$$

The scalar maps $p_{in}(\eta_{in}^k)$, $p_{out}(\eta_{out}^k)$ may be updated once after each segmentation step, if a user input is provided. The GMM of the image intensities $\psi_{in}$ and $\psi_{out}$ are re-estimated in correspondence to $\phi_\tau^k$, which determines the ROI boundaries, using expectation maximization (EM) (see: A. Dempster, N. Laird, and D. Rubin. Maximal likelihood form incomplete data via the EM algorithm. *Proceedings of the Royal Statistical Society*, 39:1-38, 1977). Therefore, $p_{in}(I;\psi_{in})$, $p_{out}(I;\psi_{out})$ may be calculated in each iteration based on the updated intensity distribution parameters.

Experimental Results

The suggested techniques may be exemplified on the segmentation of cerebral hemorrhages (CH) in human brain CT scans. CH volume estimates provided by the segmentation may be critical to the determination of the therapy procedure which may involve surgery in addition to medicine intake. It is important to note that CHs have well defined intensity range, expressed in Hounsfield units (CT numbers). Nevertheless, similar gray-level values as a result of calcification or proximity to the skull bone may fail a fully automatic segmentation process and therefore may require the insight of a physician. The disclosed user-interactive segmentation was tested by two radiology experts and compared with a commercial toolbox. The advantage of the suggested techniques was obvious, considering both operating convenience (user interaction) and accuracy (user satisfaction). Both initialization and the first stage of the segmentation process were fully automatic. As expected, not more than a single or a couple of user interaction steps were needed to complete the segmentation. High Dice scores were obtained in a comparison with independent, fully manual annotations.

An exemplification of the disclosed techniques on cerebral hemorrhages (CH) segmentation of brain CT scans is herein disclosed. Segmentation is necessary for an accurate estimate of the hemorrhage volume for further medical treatment. Scans were acquired with Philips Brilliance CT 64 system without radio contrast agents injection. The data resolution is 512×512×[90–100] with voxel size of 0.48 millimeter (mm)×0.48 mm×3 mm, with 1.5 mm overlap in the axial direction. 15 cases of CH seizures were tested.

Reference is now made to FIGS. 3A-3D, which show various views (i.e., axial, coronal, sagittal and 3D) of a CT 3D medical image of CH in a human brain of various patients (patient 1, patient 2, patient 3 and patient 4, correspondingly) segmented according to the disclosed probabilistic model. FIGS. 3A-3D present qualitative results of some of the tested cases. The fully automated segmentation (i.e., according to step 110 of the method of FIG. 1) is indicated in white dots (i.e., by a dotted boundary). The user input (i.e., user clicks according to step 120 of the method of FIG. 1) in indicated by white plus signs for false positive (i.e., indicating areas to be removed from the segmented ROI) and by white asterisks for false negative (i.e., indicating areas to be added to the segmented ROI). The final segmentation, i.e., with user interaction, is indicated by a white line (i.e., by a line boundary). For example, in the axial scan of patient 1 (i.e., in FIG. 3A), the user added asterisks in an area which was not identified by the automatic segmentation as a part of the ROI, i.e., a part of the CH. Accordingly, the dotted boundary does not include this area in the segmented ROI. However, the line boundary includes this area in the segmented ROI. In another example, the sagittal scan of patient 2 (i.e., in FIG. 3B) shows two areas identified by the automatic segmentation as part of the ROI (indicated by a dotted boundary). According to the user input, the small segmented area on the right should not be part of the ROI (i.e., is not part of the CH) and therefore indicated with plus signs. Accordingly, the line boundary does not include this area in the ROI.

Quantitative results, which were obtained with respect to manual annotation of clinical experts, are shown in Table 1 below. This includes the Dice scores (see: L. Dice. Measure of the amount of ecological association between species. *Ecology,* 26(3):297-302, 1945), sensitivity, specificity, accuracy of the segmentation results obtained by the proposed techniques.

TABLE 1

Dice, Sensitivity, Specificity and Accuracy.
Averages of 15 different slices from different patients.

| Phase vs. Score | Dice | Sensitivity | Specificity | Accuracy |
|---|---|---|---|---|
| Automatic | 0.874 ± 0.034 | 0.864 ± 0.073 | 0.99 ± 0.0019 | 0.996 ± 0.0033 |
| With user interaction | 0.905 ± 0.027 | 0.87 ± 0.063 | 0.999 ± 0.0003 | 0.997 ± 0.0022 |

In some embodiments, the disclosed interactive segmentation may be applied to medical images, which provide two dimensional (2D) information, with the required modifications. Such 2D interactive segmentation may be required, for example, when the resolution in the Z axis of a 3D medical image is very low or when the medical image is of 2D, captured by using a 2D modality, such as X-ray scans.

The present invention may be a system, a method, and/or a computer program product. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising using at least one hardware processor for:
   receiving a three-dimensional medical image of an interior volume of a patient's body;
   automatically performing three dimensional segmentation on the three dimensional medical image to detect and define a region of interest in the three dimensional medical image, wherein the performing of the three dimensional segmentation comprises automatically determining a boundary defining the region of interest;
   receiving an input from a user with respect to the three dimensional segmentation of the three dimensional medical image, wherein the input comprises spatial information indicating one or more regions of disagreement in the three-dimensional medical image with respect to the determined boundary; and
   updating the three dimensional segmentation of the three dimensional medical image based on the input received from the user, wherein the updating comprises updating the determined boundary based on the spatial information to redefine the area of interest, and wherein the updating is performed according to weights determining the relative contribution of each one of the three dimensional segmentation and the input from the user to the updating of the three dimensional segmentation, thereby determining the extent of influence of the input from the user on the determined boundary.

2. The method according to claim 1, wherein the three dimensional medical image is of an imaging modality type selected from the group consisting of: Computerized Tomography (CT), Magnetic Resonance Imaging (MM) and ultrasound.

3. The method according to claim 1, further comprising using said at least one hardware processor for performing three dimensional visualization of the segmented region of interest.

4. The method of claim 1, further comprising using said at least one hardware processor for estimating at least one measurable feature of the region of interest, wherein the at least one measurable feature is selected from the group consisting of: volume, length, width, height, pose, location and texture.

5. The method of claim 1, wherein the receiving of the input from the user and the updating of the three dimensional segmentation are performed in an iterative manner.

6. The method of claim 1, wherein the receiving of the input from the user is performed via a Graphical User Interface (GUI), and wherein the GUI presents to the user one or more views of the 3D medical image selected from the group consisting of: slice views in one or more body planes and a 3D view.

7. The method of claim 6, wherein the spatial information comprises anchors indicated by the user via a pointing device on the one or more views of the 3D medical image presented by the GUI.

8. The method of claim 1, wherein the automatically performing of the three dimensional segmentation, and the updating of the three dimensional segmentation, comprise using a probabilistic model.

9. The method of claim 8, wherein the probabilistic model is based on Gaussian Mixture Model (GMM), and wherein the GMM is used to model a distribution of the intensities of the 3D medical image within and outside of the region of interest.

10. The method of claim 8, wherein the performing of the three dimensional segmentation further comprises defining a cost functional, the cost functional comprising:
    i) an image likelihood term representing the three dimensional segmentation, and
    ii) a user interaction term representing the input from the user,
    assigning the weight of the weights determining the relative contribution of the three dimensional segmentation to the image likelihood term,
    assigning the weight of the weights determining the relative contribution of the input from the user to the user interaction term, and
    setting the weight of the weights assigned to the user interaction term to zero.

11. The method of claim 10, wherein the performing of the three dimensional segmentation and the updating the three dimensional segmentation further comprise finding a segmentation that optimizes the cost functional by using a gradient descent process.

12. A medical system comprising:
    a medical imaging device;
    at least one hardware processor configured to:
    i) automatically perform three dimensional segmentation on the three dimensional medical image to detect and define a region of interest in the three dimensional medical image, wherein the performing of the three dimensional segmentation comprises automatically determining a boundary defining the region of interest;

ii) receive an input from a user with respect to the three dimensional segmentation of the three dimensional medical image, wherein the input comprises spatial information indicating one or more regions of disagreement in the three-dimensional medical image with respect to the determined boundary; and iii) update the three dimensional segmentation of the three dimensional medical image based on the input received from the user, wherein the updating comprises updating the determined boundary based on the spatial information to redefine the area of interest, and wherein the updating is performed according to weights determining the relative contribution of each one of the three dimensional segmentation and the input from the user to the updating of the three dimensional segmentation, thereby determining the extent of influence of the input from the user on the determined boundary.

13. The medical system according to claim 12, wherein said medical imaging device is selected from the group consisting of: a Computerized Tomography (CT) device, a Magnetic Resonance Imaging (MRI) device and an ultrasound imaging device.

14. The medical system according to claim 12, wherein said at least one hardware processor is further configured to perform three dimensional visualization of the segmented region of interest.

15. The medical system of claim 12, wherein said at least one hardware processor is further configured to estimate at least one measurable feature of the region of interest, wherein the at least one measurable feature is selected from the group consisting of: volume, length, width, height, pose, location and texture.

16. The medical system of claim 12, wherein the receiving of the input from the user and the updating of the three dimensional segmentation are performed in an iterative manner.

17. The medical system of claim 12, wherein the receiving of the input from the user is performed via a GUI, and wherein the GUI presents to the user one or more views of the 3D medical image selected from the group consisting of: slice views in one or more body planes and a 3D view.

18. The medical system of claim 17, wherein the spatial information comprises anchors indicated by the user via a pointing device on the one or more views of the 3D medical image presented by the GUI.

19. The medical system of claim 12, wherein the automatically performing of the three dimensional segmentation, and the updating of the three dimensional segmentation, comprise using a probabilistic model, wherein the probabilistic model is based on Gaussian Mixture Model (GMM), and wherein the GMM is used to model a distribution of the intensities of the 3D medical image within and outside of the region of interest.

20. The medical system of claim 19, wherein the performing of the three dimensional segmentation further comprises defining a cost functional, the cost functional comprising:

i) an image likelihood term representing the three dimensional segmentation, and ii) a user interaction term representing the input from the user, assigning the weight of the weights determining the relative contribution of the three dimensional segmentation to the image likelihood term, assigning the weight of the weights determining the relative contribution of the input from the user to the user interaction term, and setting the weight of the weights assigned to the user interaction term to zero.

* * * * *